US010330622B2

(12) United States Patent
Noel et al.

(10) Patent No.: US 10,330,622 B2
(45) Date of Patent: Jun. 25, 2019

(54) GLASS-SEALED ELECTRODE

(71) Applicant: OneSubsea IP UK Limited, London (GB)

(72) Inventors: Jean-Francois Noel, Søreidgrend (NO); Emmanuel Lagrand, Bergen (NO)

(73) Assignee: ONESUBSEA IP UK LIMITED, London (GB)

(*) Notice: Subject to any disclaimer, the term of this patent is extended or adjusted under 35 U.S.C. 154(b) by 0 days.

(21) Appl. No.: 15/646,416

(22) Filed: Jul. 11, 2017

(65) Prior Publication Data
US 2019/0017952 A1 Jan. 17, 2019

(51) Int. Cl.
*G01N 27/07* (2006.01)
*G01N 27/22* (2006.01)
*G01R 27/26* (2006.01)
*G01N 33/28* (2006.01)
*C03C 19/00* (2006.01)

(52) U.S. Cl.
CPC .......... *G01N 27/07* (2013.01); *G01N 27/221* (2013.01); *G01N 27/226* (2013.01); *G01N 33/2823* (2013.01); *G01R 27/2617* (2013.01); *C03C 19/00* (2013.01)

(58) Field of Classification Search
CPC ................................................. G01R 27/2617
See application file for complete search history.

(56) References Cited

U.S. PATENT DOCUMENTS

| | | | |
|---|---|---|---|
| 2,525,754 A | 10/1950 | Albrecht | |
| 4,388,834 A * | 6/1983 | Schmoock | G01F 1/584 73/861.12 |
| 4,831,470 A | 5/1989 | Brunnett et al. | |
| 5,675,259 A * | 10/1997 | Arndt | G01F 1/66 324/642 |
| 2003/0011386 A1 | 1/2003 | Xie et al. | |
| 2005/0057243 A1 | 3/2005 | Johnson et al. | |
| 2010/0321046 A1 | 12/2010 | Randall et al. | |
| 2011/0056402 A1 | 3/2011 | Gustabsson et al. | |
| 2015/0090004 A1 * | 4/2015 | Noel | H01B 17/30 73/37 |
| 2016/0169720 A1 | 6/2016 | Xie et al. | |
| 2017/0052167 A1 | 2/2017 | Eriksson et al. | |

FOREIGN PATENT DOCUMENTS

DE 2742416 B1 9/1978
WO 2015049592 A2 4/2015

OTHER PUBLICATIONS

Partial Search Report issued in European Patent Appl. No. 18182702.3 dated Nov. 6, 2018; 15 pages.
European Extends Search Report for EP Application No. 181827023 dated Feb. 22, 2019; 15 pgs.

* cited by examiner

*Primary Examiner* — Clayton E. LaBalle
*Assistant Examiner* — Jas A Sanghera
(74) *Attorney, Agent, or Firm* — Fletcher Yoder, P.C.

(57) ABSTRACT

An electrode includes a conductor, an insulator, and a housing. The insulator is positioned at least partially around the conductor. The housing is positioned at least partially around the conductor. An upper surface of the insulator may be at least partially concave, an outer surface of the housing may have a groove formed therein, or both.

20 Claims, 12 Drawing Sheets

GLASS-SEALED ELECTRODE

BACKGROUND

A glass-sealed electrode may be used to measure the frequency-dependent complex permittivity of a process fluid mixture at a selected frequency. When used in the oilfield, the electrode may be installed in direct contact with production fluids in topside or subsea applications. The electrode may also be used on tools that are run into a wellbore.

The electrode may include a conductor, a glass insulator, and a metal housing. The glass insulator may have a flat, grinded upper surface configured to be exposed to the process fluid. The flat, grinded upper surface is designed to be flush with a wall of a tubular member (e.g., a pipe) to have optimal contact with the fluid layer. However, the flat, grinded upper surface may lead to defects in the electrode. More particularly, it may lead to cracks in the upper surface of the glass insulator and/or spalling of the glass insulator. As a result, it would be desirable to have an improved electrode that is resistant to cracks and/or spalling.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

An electrode is disclosed. The electrode is configured to measure a frequency-dependent complex permittivity of a fluid. The electrode includes a conductor, an insulator, and a housing. The insulator is positioned at least partially around the conductor. An upper surface of the insulator is at least partially concave. The housing is positioned at least partially around the insulator.

In another embodiment, the electrode includes a conductor, an insulator, and a housing. The insulator is positioned at least partially around the conductor. The housing is positioned at least partially around the insulator. An outer surface of the housing may have a groove formed therein.

A method of producing an electrode is also disclosed. The method includes positioning a conductor at least partially within an insulator. The method also includes positioning the insulator at least partially within a housing. The method also includes shrink-fitting the conductor, the insulator, and the housing, or a combination thereof together. The method also includes forming a groove in an outer surface of the housing. The method may also or instead includes causing an upper surface of the insulator to be substantially concave.

BRIEF DESCRIPTION OF THE DRAWINGS

The accompanying drawings, which are incorporated in and constitute a part of this specification, illustrate embodiments of the present teachings and together with the description, serve to explain the principles of the present teachings. In the figures.

DETAILED DESCRIPTION

Reference will now be made in detail to specific embodiments illustrated in the accompanying drawings and figures. In the following detailed description, numerous specific details are set forth in order to provide a thorough understanding of the invention. However, it will be apparent to one of ordinary skill in the art that embodiments may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object could be termed a second object, and, similarly, a second object could be termed a first object, without departing from the scope of the present disclosure.

The terminology used herein is for the purpose of describing particular embodiments only and is not intended to be limiting. As used in the description and the appended claims, the singular forms "a," "an" and "the" are intended to include the plural forms as well, unless the context clearly indicates otherwise. It will also be understood that the term "and/or" as used herein refers to and encompasses any and possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, operations, elements, components, and/or groups thereof. Further, as used herein, the term "if" may be construed to mean "when" or "upon" or "in response to determining" or "in response to detecting," depending on the context.

Figure 1:
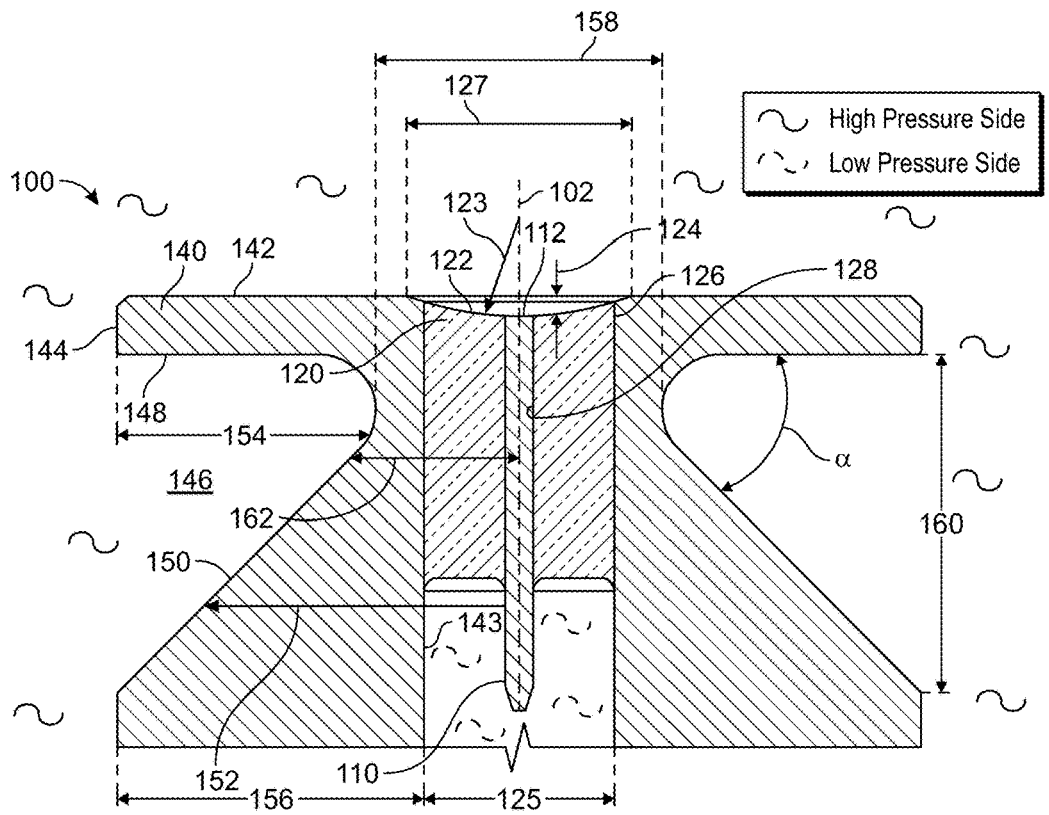
FIG. 1 is a cross-sectional side view of an electrode, according to some embodiments.

FIG. 1 is a cross-sectional side view of an electrode (also referred to as a probe) 100, according to some embodiments. The electrode 100 may be an open, coaxial, glass-sealed electrode. The electrode 100 may include a conductor 110, an insulator 120, and a housing 140.

The electrode 100 may be used to measure a frequency-dependent complex permittivity of a (e.g., multi-phase) process fluid mixture at a selected frequency. More particularly, an electromagnetic wave may be transmitted through the electrode 100, and the wave is reflected when it meets the open end of the electrode 100. The difference in amplitude and phase of the reflected wave is then measured. When fluids wet the surface of the insulator 120, the electrode 100 may modify the impedance between the conductor 110 and the housing 140. This may result in a change of amplitude and phase of the reflected wave. The change of impedance, and therefore reflected wave amplitude and phase, may depend on the characteristics of the fluid wetting the insulator 120. This allows a user to characterize the type and properties of the fluid which is wetting the insulator 120. The complex permittivity may then be used to estimate the conductivity and/or salinity of water in the process fluid. The complex permittivity may also be used to detect liquid water in the process fluid. The electrode 100 may be used at pressures up to about 345 MPa and at temperatures up to about 300° C. The portions of the electrode 100 that may be exposed to high and low pressures are shown in FIG. 1.

As shown, the conductor 110 may be positioned at least partially within the insulator 120, and the insulator 120 may be positioned at least partially within the housing 140. In at least one embodiment, the conductor 110, the insulator 120, and the housing 140 may be coaxial (i.e., concentric) with one another about a central longitudinal axis 102 through the electrode 100. The conductor 110 may be a pin made of an electrically-conductive material such as a metal, a conductive ceramic, a cemented carbide, or a cermet. The conductor 110 may have a high resistivity and a low dielectric constant to minimize the size of the electrode 100. The conductor 110 may conduct electrons with a low electrical resistivity (e.g., to limit loss of signal). The insulator 120 may be made of glass (e.g., borosilicate). The insulator 120 may prevent the flow of electrons between the conductor 110 and housing 140. The housing 140 may be made of metal, allowing the housing 140 to conduct electrons. As such, the housing 140 may have a low electrical resistivity. The housing 140 may also induce compression on the conductor 110 and/or the insulator 120 while cooling after firing. The compression on the conductor 110 may prevent the conductor 110 from being pushed out under high differential pressure. The compression on the insulator 120 may reduce or limit the tensile stresses in the insulator 120. The conductor 110, the insulator 120, and/or the housing 140 may be sealed together by wetting and shrink fitting (e.g., by firing), as described in more detail below.

The insulator 120 may be substantially cylindrical with a bore formed axially-therethrough for receiving the conductor 110. An upper surface 122 of the insulator 120 may be configured to be in fluid communication with the high pressure portion of the process fluid. The lower surface of the insulator 120 may not be in fluid communication with the process fluid. Instead, the lower surface may be in fluid communication with air, nitrogen, or another inert gas, which may have a lower pressure (e.g., 100 kPa). In contrast to conventional insulators that have an upper surface that is substantially flat (i.e., in a plane that is perpendicular to the central longitudinal axis 102), the upper surface 122 of the insulator 120 may not be flat. Rather, the upper surface 122 may be substantially concave, as shown in FIG. 1. This concave shape may reduce the tension stresses exerted on the upper surface 122 of the insulator 120 by the process fluid during measurements when compared to the flat, grinded upper surface of the conventional insulator. This may reduce or prevent cracks and/or spalling in the (e.g., insulator 120 of the) electrode 100.

In at least one embodiment, the concave shape may be or include a curve (e.g., a hyperbola, a parabola, an ellipse, a circle, or a combination thereof). For example, the concave shape may include a radius of curvature 123. Thus, an inner (e.g., radial) portion 128 of the upper surface 122 of the insulator 120 may be recessed with respect to an outer (e.g., radial) portion 126 of the upper surface 122 of the insulator 120 (or an upper surface 142 of the housing 140). A depth 124 of the recess may increase proceeding (e.g., radially) inward toward the central longitudinal axis 102. The maximum depth 124 may be from about 0.05 mm to about 0.5 mm or about 0.1 mm to about 0.3 mm (e.g., proximate to the central longitudinal axis 102). The depth 124 may be measured parallel to the central longitudinal axis 102 through the electrode 100.

An upper end 112 of the conductor 110 may be substantially aligned with the inner (e.g., radial) portion 128 of the upper surface 122 of the insulator 120. Thus, the upper end 112 of the conductor 110 may be recessed from the outer (e.g., radial) portion 126 of the upper surface 122 of the insulator 120 (or the upper surface 142 of the housing 140) by the distance 124.

The housing 140 may be cylindrical with a bore formed axially-therethrough for receiving the insulator 120. In at least one embodiment, the upper surface 142 of the housing 140 may also include at least a portion of the concave shape (e.g., surrounding the insulator 120). This portion of the concave shape in the upper surface 142 of the housing 140 may include the same radius of curvature 123 as the upper surface 122 of the insulator 120. Thus, as shown, the outer (e.g., radial) portion 126 of the upper surface 122 of the insulator 120 may be recessed with respect to the upper surface 142 of the housing 140. In addition, a (grinding) diameter 127 of the concave shape in the upper surface 142 housing 140 may be from about 100% to about 130% of the diameter 125 of the insulator 120.

In contrast to conventional housings, the outer surface 144 of the housing 140 may define one or more (e.g., radial) groove(s) 146 that extend(s) at least partially around a circumference of the outer surface 144 of the housing 140. The groove 146 may reduce the tension stresses exerted on the upper surface 122 of the insulator 120 by the process fluid during measurements when compared to the entirely cylindrical outer surface of the conventional insulator. This may reduce or prevent cracks and/or spalling in the (e.g., insulator 120 of the) electrode 100.

A first portion 148 of the outer surface 144 may be substantially perpendicular to the central longitudinal axis 102, and a second portion 150 of the outer surface 144 may be oriented at an angle α with respect to the central longitudinal axis 102. The angle α may be from about 20° to about 70°, about 30° to about 60°, or about 40° to about 50°. A (e.g., radial) distance 152 between the central longitudinal axis 102 and the second portion 150 may increase proceeding away from the upper surface 142 of the housing 140. A transition between the first and second portions 148, 150 may include a radius of curvature that is from about 10% to about 25% of a height 160 of the groove 146.

A maximum width 154 of the groove 146 may be from about 80% to about 90% of a maximum width 156 between an inner surface 143 of the housing 140 and the outer surface 144 of the housing 140. A distance 162 between the central longitudinal axis 102 and an innermost radial surface of the housing 140 defining the groove 146 may be from about 100% to about 130% of the diameter 125 of the insulator 120. A groove depth diameter 158 may be from about 110% to about 300% of the diameter 125 of the insulator 120.

Figure 2A:
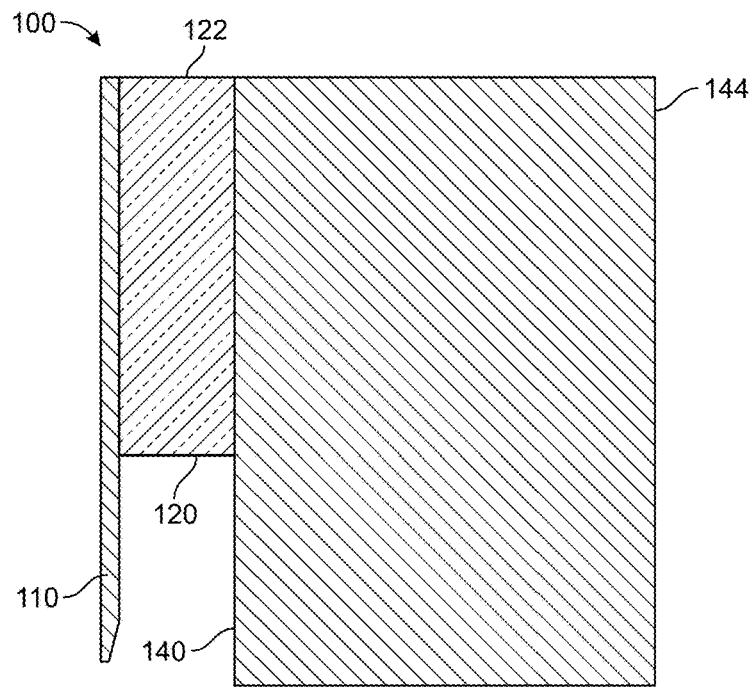
FIG. 2A is a cross-sectional side view of the electrode showing an insulator having a flat upper surface and a housing with no groove formed therein, according to some embodiments.
Figure 3A:
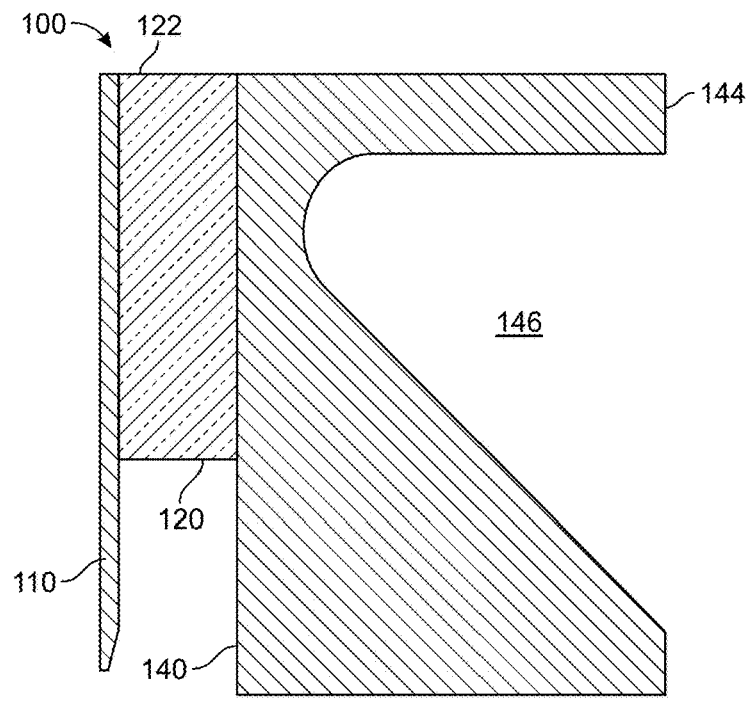
FIG. 3A is a cross-sectional side view of the electrode showing the insulator having a flat upper surface and the housing with a groove formed therein, according to some embodiments.
Figure 4A:
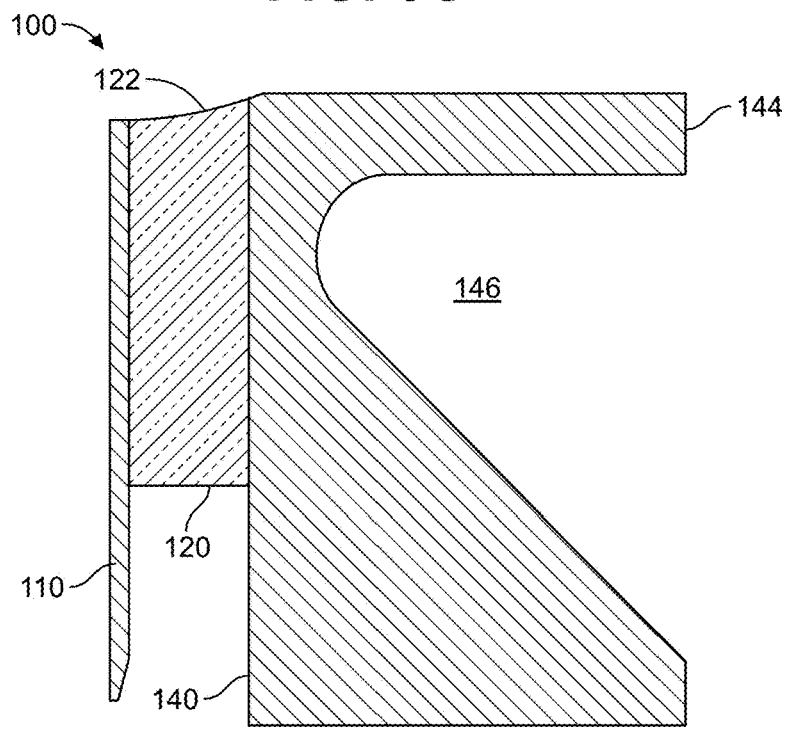
FIG. 4A is a cross-sectional side view of the electrode showing the insulator having a concave upper surface and the housing having a groove formed therein, according to some embodiments.

FIGS. 2A, 3A, and 4A are cross-sectional side views of the electrode 100 with a flat upper surface 122 of the insulator 120 and no groove 146 in the housing 140 (FIG. 2A), with a flat upper surface 122 of the insulator 120 and the groove 146 in the housing 140 (FIG. 3A), and with a concave upper surface 122 of the insulator 120 and the groove 146 in the housing 140 (FIG. 4A), according to some embodiments.

Figure 2B:
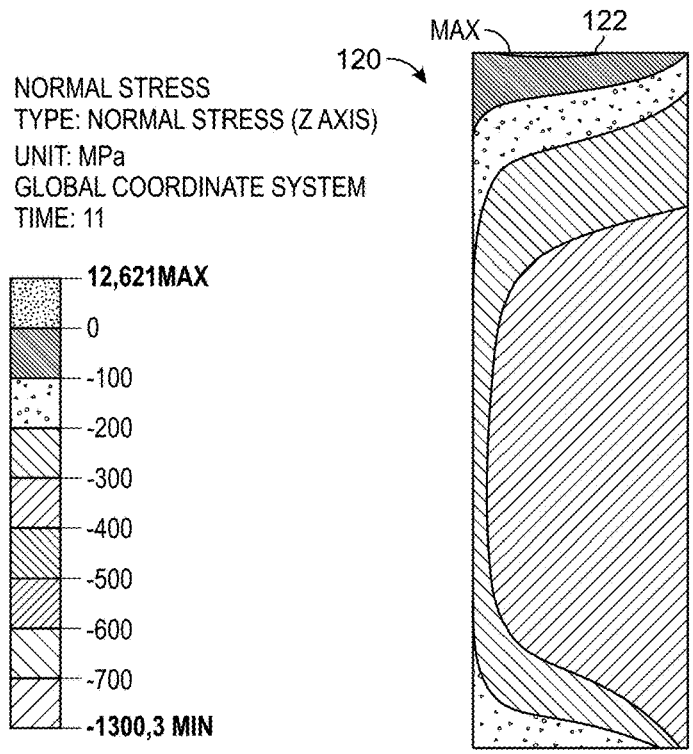
FIG. 2B is a finite element analysis (FEA) of the insulator of the electrode in FIG. 2A after the components of the electrode are shrink-fit together and before the components are welded together, according to some embodiments.
Figure 2C:
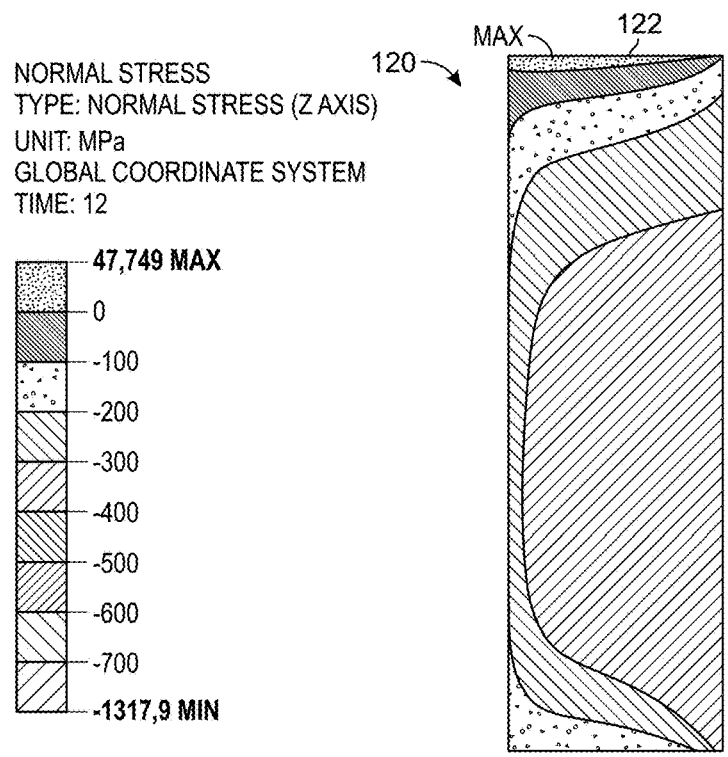
FIG. 2C is a finite element analysis of the insulator of electrode in FIG. 2A after the components of the electrode are shrink-fit and welded together, according to some embodiments.

FIGS. 2B and 2C show finite element analyses (FEA) of the insulator 120 of the electrode 100 in FIG. 2A after the conductor 110, the insulator 120, and the housing 140 are shrink-fit together (FIG. 2B) and after the conductor 110, the insulator 120, and the housing 140 are welded together (FIG. 2C), according to some embodiments. The stresses in FIG. 2B may be due to the manufacturing process (e.g., shrink-fitting of the insulator 120). After shrink-fitting, the insulator 120 may contain some tensile stresses. In FIG. 2C, the insulator 120 may have increased tensile stresses due to the subsequent welding (e.g., after manufacturing). As shown in FIG. 2B, the stress experienced proximate to the upper surface 122 of the insulator 120 is more than 12 MPa after the conductor 110, the insulator 120, and/or the housing 140 are shrink-fit together by firing. As shown in FIG. 2C, the stress experienced proximate to the upper surface 122 of the insulator 120 is more than 47 MPa after the conductor 110, the insulator 120, and/or the housing 140 are subsequently welded together.

Figure 3B:
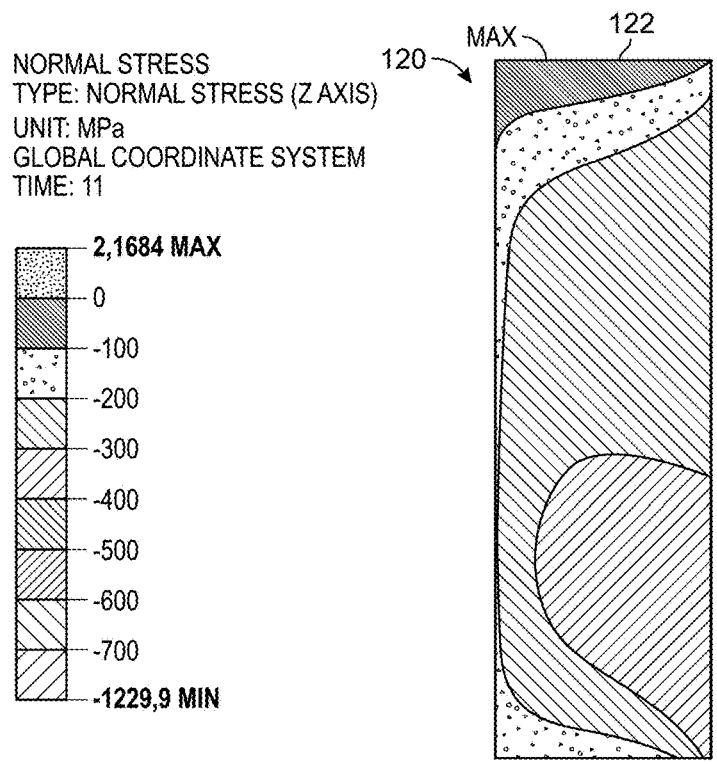
FIG. 3B is a finite element analysis of the insulator of electrode in FIG. 3A after the components of the electrode are shrink-fit together and before the components are welded together, according to some embodiments.
Figure 3C:
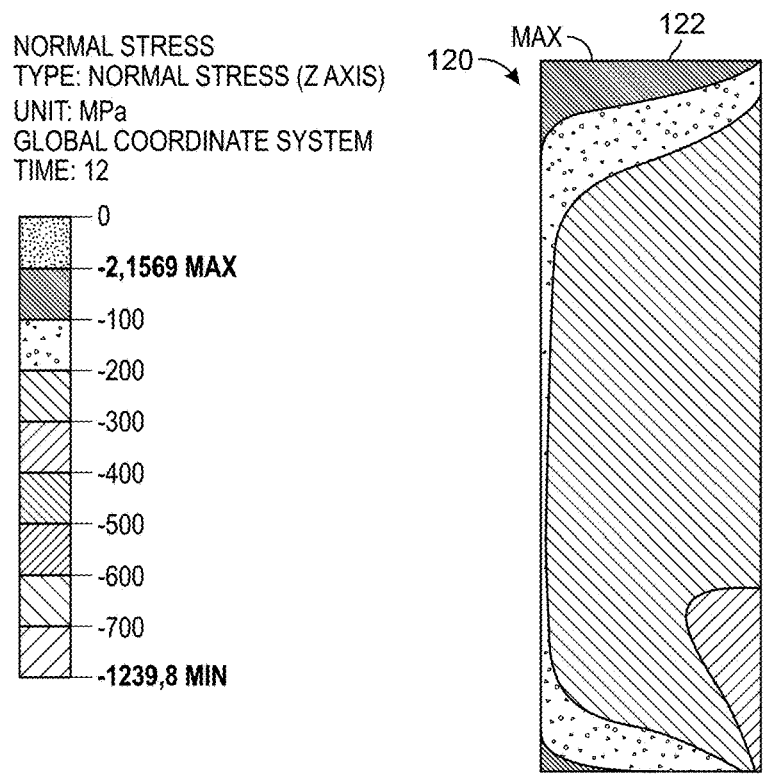
FIG. 3C is a finite element analysis of the insulator of electrode in FIG. 3A after the components of the electrode are shrink-fit and welded together, according to some embodiments.

FIGS. 3B and 3C show finite element analyses of the insulator 120 of the electrode 100 in FIG. 3A after the conductor 110, the insulator 120, and the housing 140 are shrink-fit together (FIG. 3B) and after the conductor 110, the insulator 120, and the housing 140 are welded together (FIG. 3C), according to some embodiments. As shown in FIG. 3B, forming the groove 146 in the housing 140 may reduce the stress experienced proximate to the upper surface 122 of the insulator 120 to about 2.2 MPa after the conductor 110, the insulator 120, and/or the housing 140 are shrink-fit together by firing. As shown in FIG. 3C, forming the groove 146 in the housing 140 may reduce the stress experienced proximate to the upper surface 122 of the insulator 120 to about −2.2 MPa after the conductor 110, the insulator 120, and/or the housing 140 are subsequently welded together. A positive stress value indicates a tensile stress, and a negative stress value indicates a compressive stress. The insulator 120 may have electrical properties like high resistivity and low dielectric constant that are found in materials like glass or ceramic or glass-ceramic. These are brittle materials and therefore exhibit high compression strength but low tensile strength. Therefore, a low (or zero) tensile stress in the insulator 120 may prevent the insulator 120 from cracking.

Figure 4B:
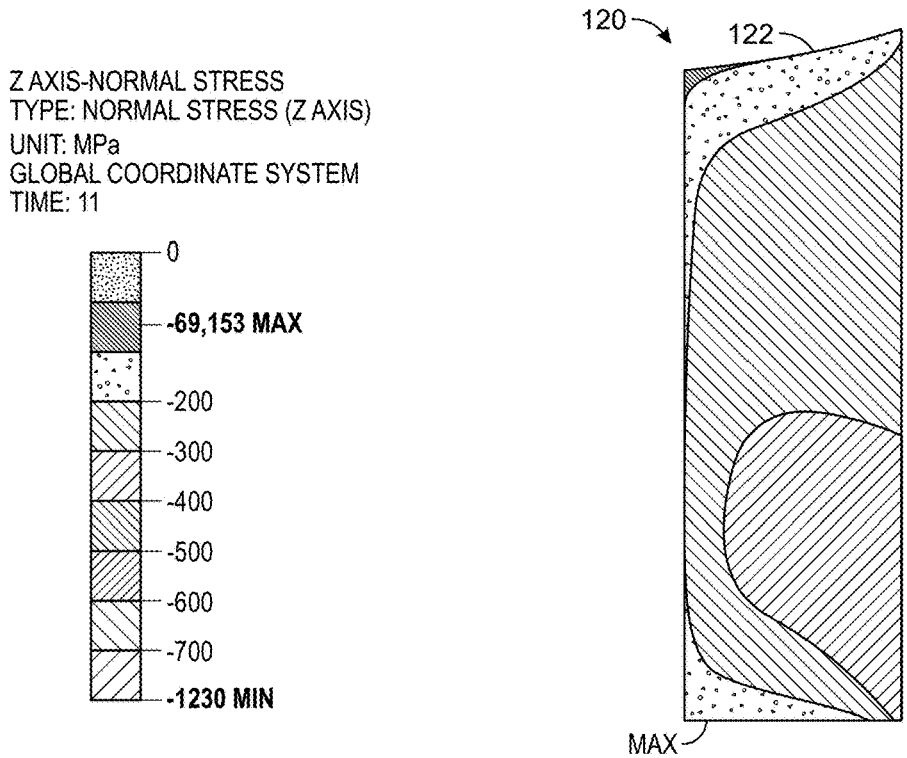
FIG. 4B is a finite element analysis of the insulator of electrode in FIG. 4A after the components of the electrode are shrink-fit together and before the components are welded together, according to some embodiments.
Figure 4C:
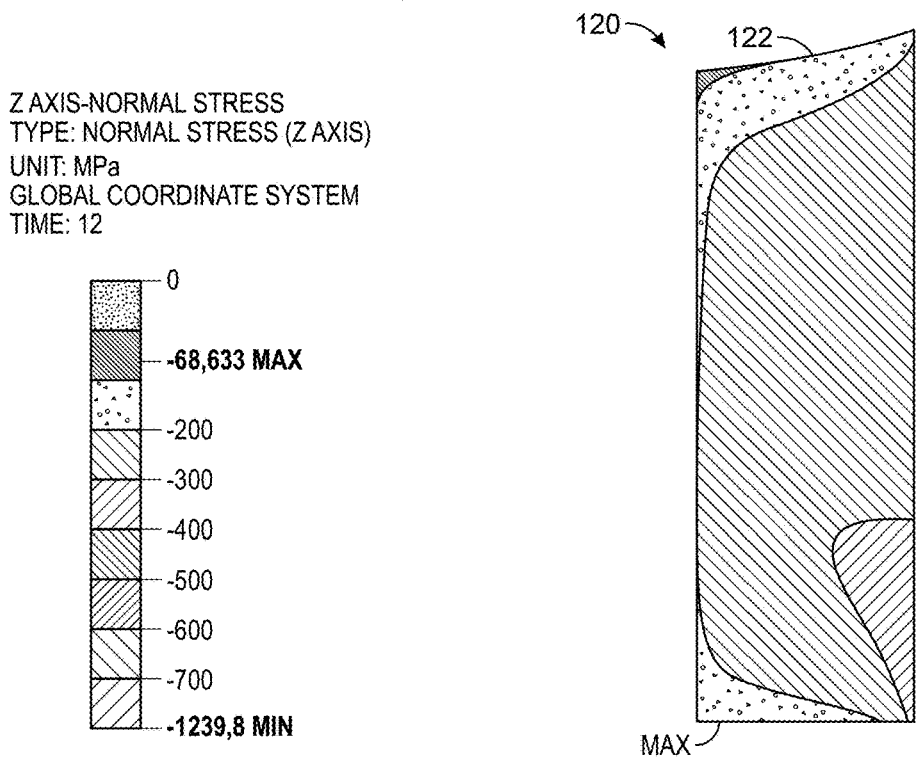
FIG. 4C is a finite element analysis of the insulator of electrode in FIG. 4A after the components of the electrode are shrink-fit and welded together, according to some embodiments.

FIGS. 4B and 4C show finite element analyses of the insulator 120 of the electrode 100 in FIG. 4A after the conductor 110, the insulator 120, and the housing 140 are shrink-fit together (FIG. 4B) and after the conductor 110, the insulator 120, and the housing 140 are welded together (FIG. 4C), according to some embodiments. As shown in FIG. 4B, making the upper surface 122 of the insulator 120 concave and forming the groove 146 in the housing 140 may reduce the stress experienced proximate to the upper surface 122 of the insulator 120 to about −69 MPa after the conductor 110, the insulator 120, and/or the housing 140 are shrink-fit together by firing. As shown in FIG. 4C, making the upper surface 122 of the insulator 120 concave and adding the groove 146 in the housing 140 may reduce the stress experienced proximate to the upper surface 122 of the insulator 120 to about −69 MPa after the conductor 110, the insulator 120, and/or the housing 140 are subsequently welded together.

Figure 5A:
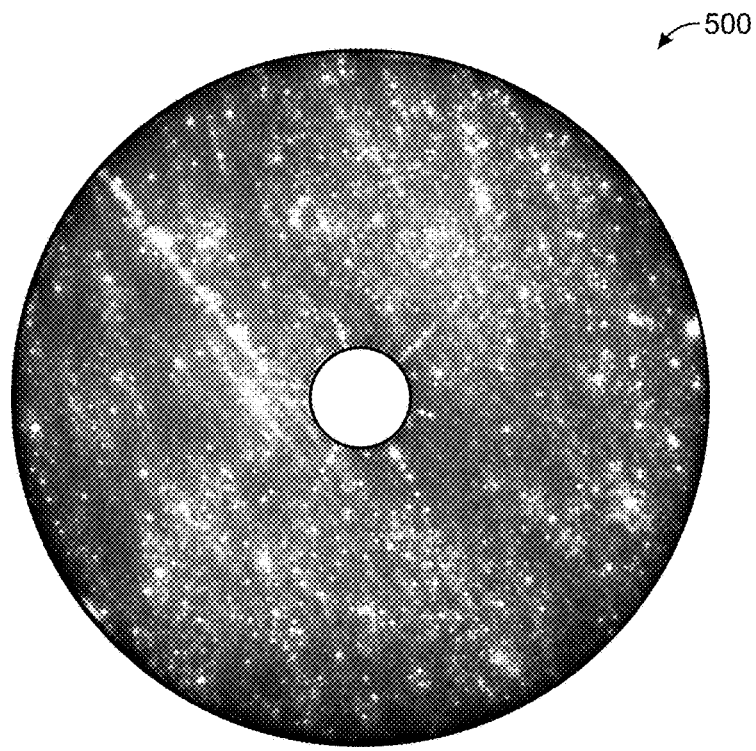
FIG. 5A is a photograph of an upper surface of an insulator of an electrode being inspected by a fluorescent penetrant inspection (FPI), according to some embodiments. The insulator of the electrode in FIG. 5A has a flat upper surface, and the housing of the electrode has no groove formed therein.
Figure 5B:
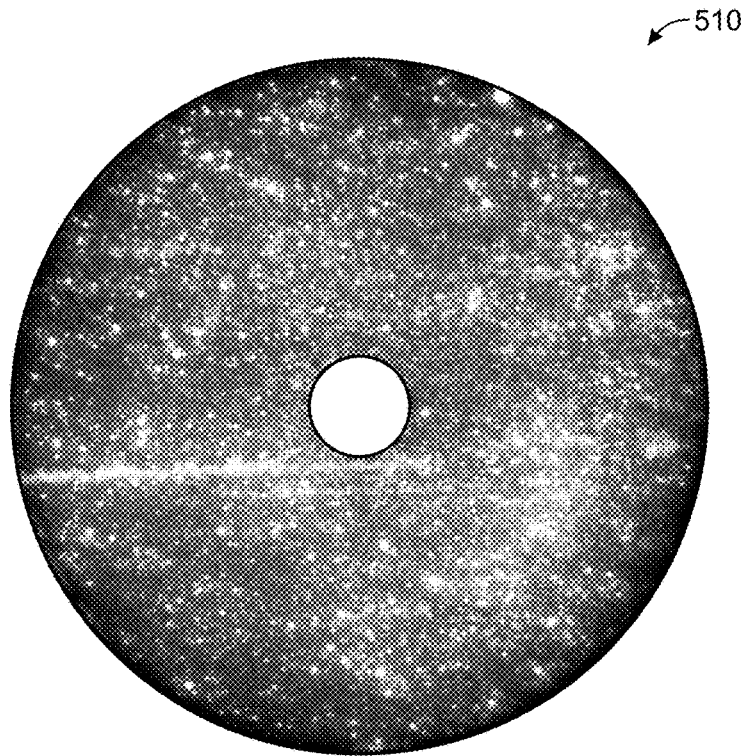
FIG. 5B is a photograph of the upper surface of the insulator from FIG. 5A being inspected by the FPI after a groove is formed in the housing, according to some embodiments.

FIGS. 5A and 5B are photographs 500, 510 of an upper surface of an insulator of an electrode being inspected by a fluorescent penetrant inspection (FPI) before and after the groove is formed in the housing, respectively, according to some embodiments. The photographs 500, 510 taken in FIGS. 5A and 5B were taken after a pressure test at 15 ksi (103 MPa). As shown in FIG. 5A, cracks are clearly apparent in the insulator when no groove is formed in the housing. However, as shown in FIG. 5B, there are fewer and smaller cracks in the insulator after the groove is formed in the housing. This is because the tensile stresses at the surface become compressive stresses that may "close" the cracks, making them less visible.

More particularly, the groove may promote compression in the insulator at two stages of the fabrication. First, during firing of the insulator into the housing, due to a thermal expansion difference between the insulator and the housing, radial compression will be induced on the insulator. However, in the meantime, the difference in thermal expansion may also induce stresses at the top and bottom of the insulator due to the difference in shrinkage in the axial direction. The radial shrinkage may desirable, but the axial shrinkage may not be. Adding the groove in the housing may limit the tensile stresses generated at the top of the insulator due to the axial shrinkage without reducing the radial compression at the top. The groove may also serve a second purpose after the insulator has been fired (e.g., after welding the electrode to the rest of the measurement equipment). After welding, when the melted metal cools down, it shrinks. This induces residual stresses that can propagate from the weld location up to the top face of the insulator. Introducing the groove in the housing may redistribute the residual stresses from welding to other locations. In other words the groove limits the stresses at the top of the insulator that would be induced by welding.

Figure 6A:
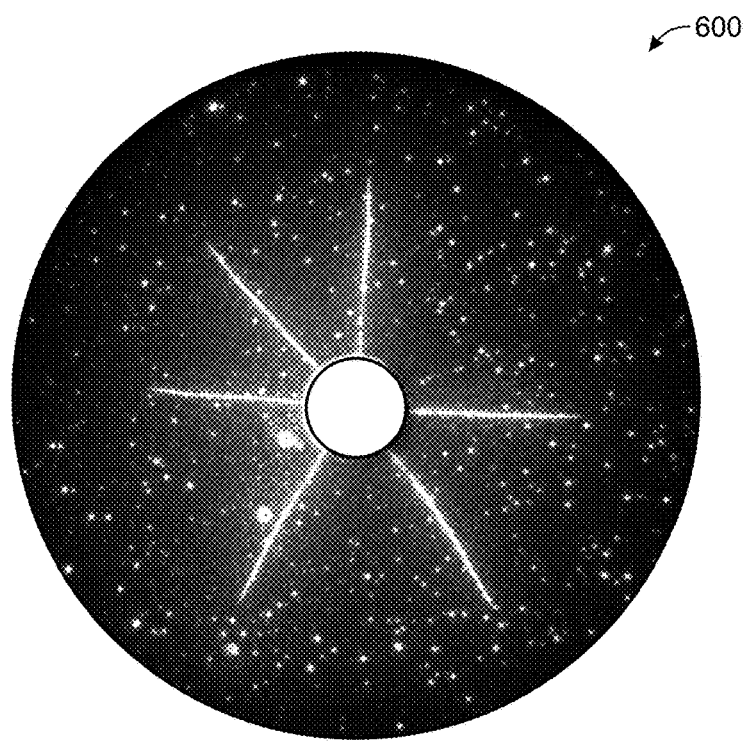
FIG. 6A is a photograph of an upper surface of an insulator of an electrode being inspected by the FPI after welding and a pressure test (at 15 ksi; 103 MPa), according to some embodiments. The insulator of the electrode in FIG. 6A has a flat upper surface, and the housing of the electrode has no groove formed therein.
Figure 6B:
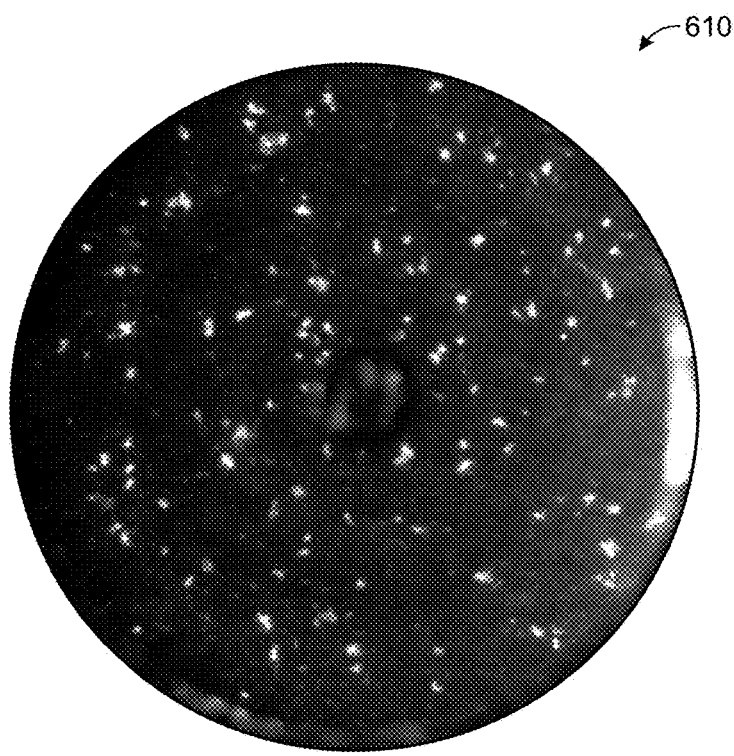
FIG. 6B is a photograph of an upper surface of an insulator of an electrode being inspected by the FPI after welding and a pressure test (at 15 ksi; 103 MPa), according to some embodiments. The insulator of the electrode in FIG. 6B has a concave upper surface, and the housing of the electrode has a groove formed therein.

FIGS. 6A and 6B are photographs 600, 610 of upper surfaces of insulators of electrodes being inspected by the FPI, according to some embodiments. The insulator of the electrode in FIG. 6A has a flat upper surface, and the housing of the electrode has no groove formed therein. The insulator of the electrode in FIG. 6B has a concave upper surface, and the housing of the electrode has a groove formed therein. The photographs 600, 610 taken in FIGS. 6A and 6B were taken after welding and a pressure test at 15 ksi (103 MPa). As shown in FIG. 6A, cracks are clearly apparent in the insulator of the electrode that has no groove formed in the housing. However, as shown in FIG. 6B, there are no cracks in the insulator of the electrode that has the groove formed in the housing. This may be because the insulator in the electrode in FIG. 6B is under more compression due to the concave upper surface of the insulator and the groove in the housing.

Figure 7:
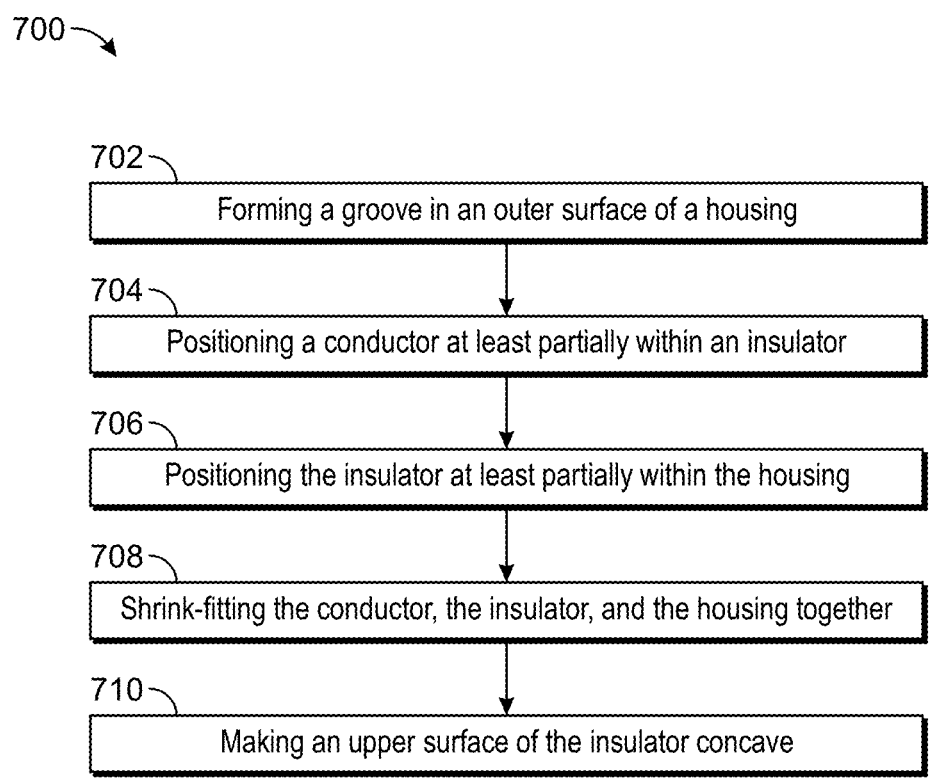
FIG. 7 is a flowchart of a method for producing the electrode, according to some embodiments.

FIG. 7 is a flowchart of a method 700 for producing the electrode 100, according to some embodiments. The method 700 may also include forming one or more grooves 146 in the outer surface 144 of the housing 140, as at 702. The method 700 may include positioning the conductor 110 at least partially within the insulator 120, as at 704. The method 700 may also include positioning the insulator 120 at least partially within the housing 140, as at 706. At this point, the insulator 120 may have a slightly bigger inner diameter than the conductor 110 and a slightly smaller outer diameter than the inner diameter of the housing 140 to allow the assembly.

The method 700 may also include shrink-fitting the conductor 110, the insulator 120, and/or the housing 140 together (e.g., by firing), as at 708. More particularly, the conductor 110, the insulator 120, and the housing 140 are heated up together until the viscosity of the insulator 120 (e.g., made of glass) is low enough for the insulator 120 to fill up the free space. Then, the conductor 110, the insulator 120, and the housing 140 are cooled. While cooling, due to the differential thermal expansion between the materials, the housing 140 may compress the insulator 120 (i.e., shrink-fitting), and the insulator 120 may in turn compress the conductor 110.

The method 700 may also include forming a concave upper surface 122 of the insulator 120, as at 710. The concave shape may be formed by grinding the upper surface 122 before or after the positioning and/or the shrink-fitting. In at least one embodiment, greater than about 70%, greater than about 80%, greater than about 90%, or about 100% of the surface area of the upper surface 122 may be grinded to form a substantially inverted dome-shaped upper surface 122. In at least one embodiment, the groove 146 in the housing 140 may be formed before the upper surface 122 of the insulator 120 is made to be concave. In at least one embodiment, the groove 146 in the housing 140 or the concave shape of the upper surface 122 of the insulator 120 may be omitted.

Figure 8:
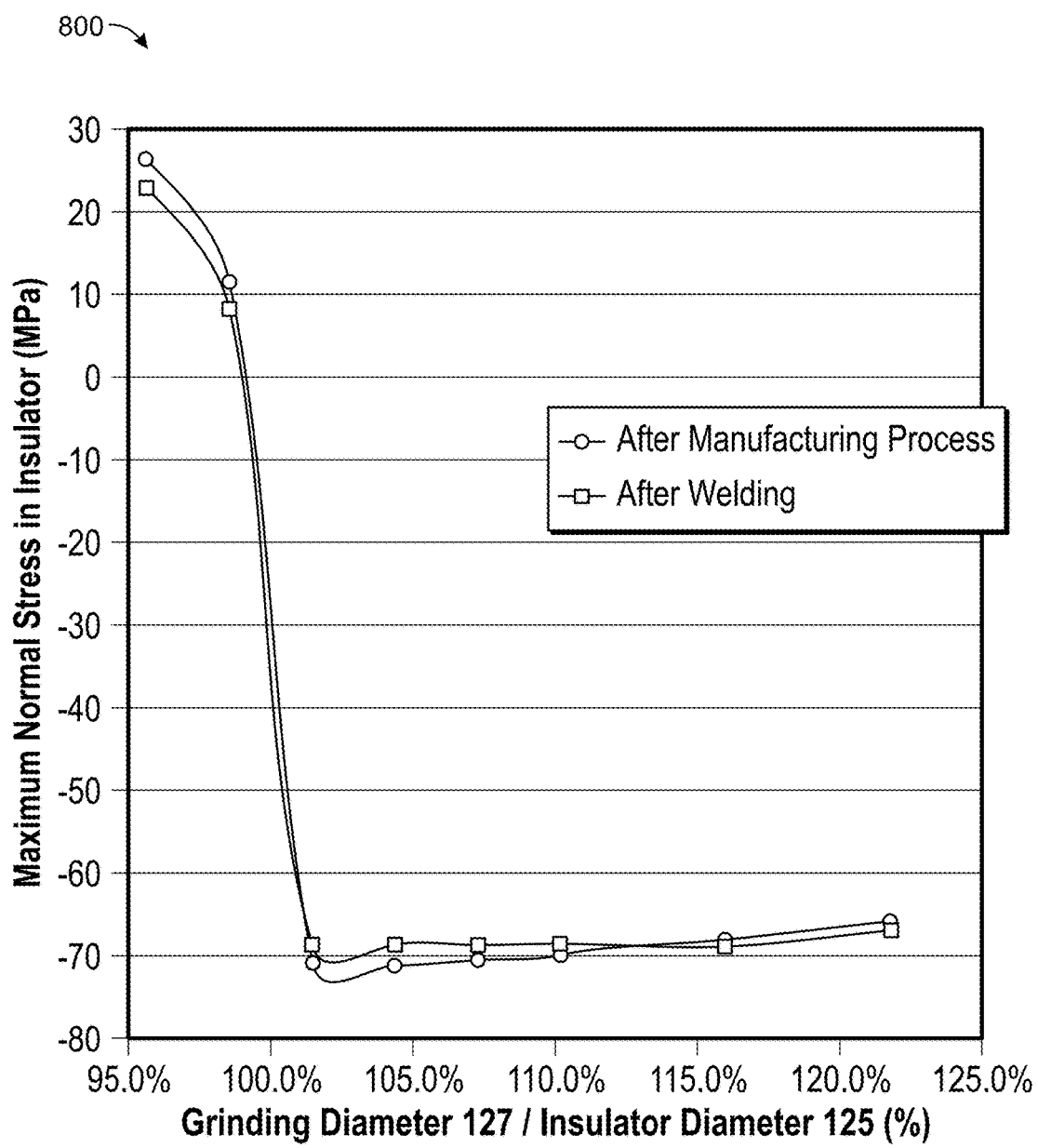
FIG. 8 is a graph showing a grinding diameter/insulator diameter vs. maximum normal stress in the insulator, according to some embodiments.

FIG. 8 is a graph 800 showing a ratio of the grinding diameter 127 to insulator diameter 125 vs. maximum normal stress in the insulator 120, according to some embodiments. The ratio may influence the strain/stress distributions within the insulator 120. To improve the stress distributions, the ratio may be from about 102% to about 122%.

Figure 9:
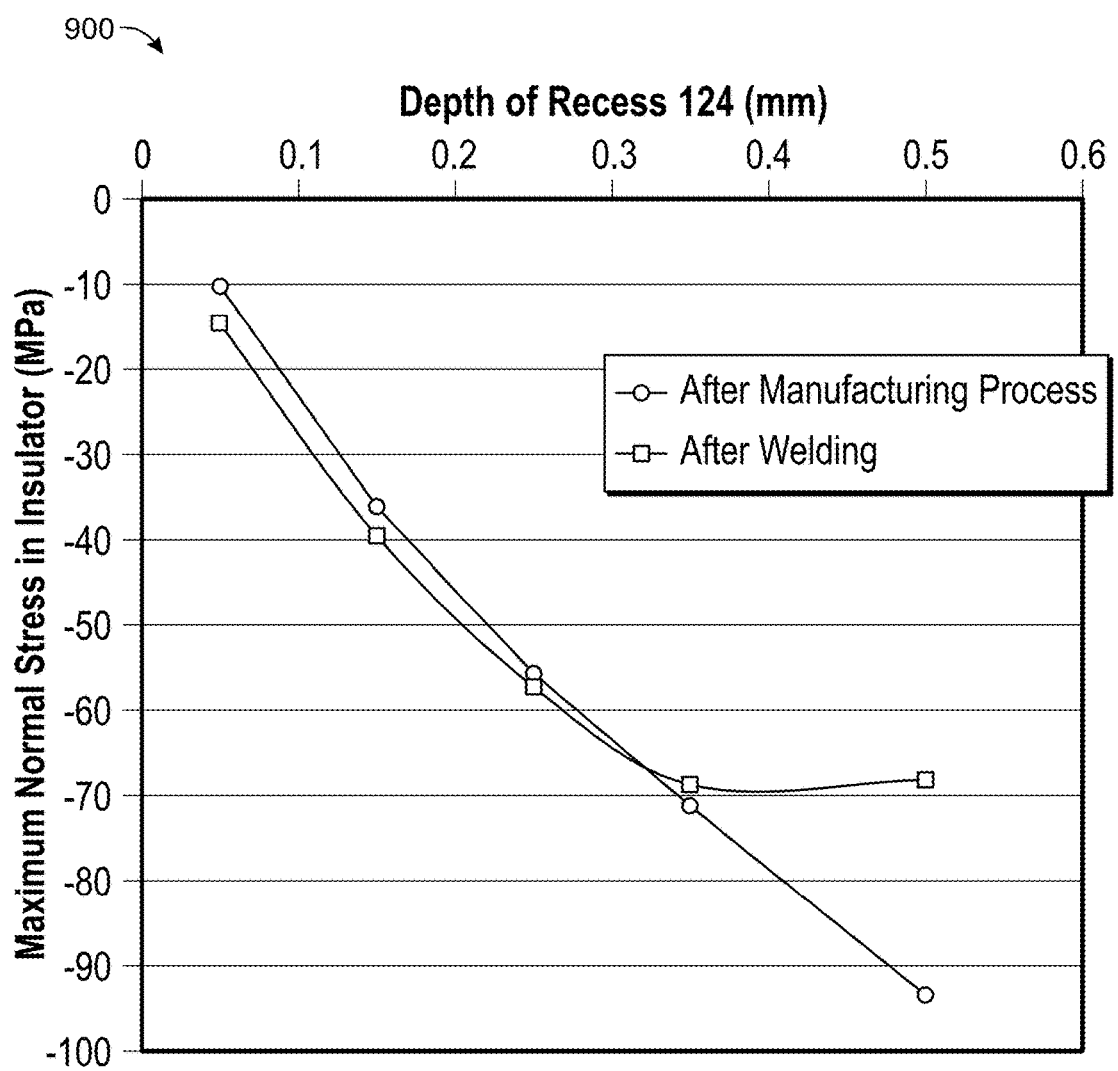
FIG. 9 is a graph showing a depth of the recess vs. the maximum normal stress in the insulator, according to some embodiments.

FIG. 9 is a graph 900 showing a depth of the recess 124 vs. the maximum normal stress in the insulator 120, according to some embodiments. The depth of the recess 124 may also influence the strain/stress distributions within the insulator 120. To improve the stress distributions, the depth of the recess 124 may be from about 0.1 mm to about 0.5 mm, about 0.2 mm to about 0.5 mm, about 0.3 mm to about 0.5 mm, or about 0.4 mm to about 0.5 mm.

Figure 10:
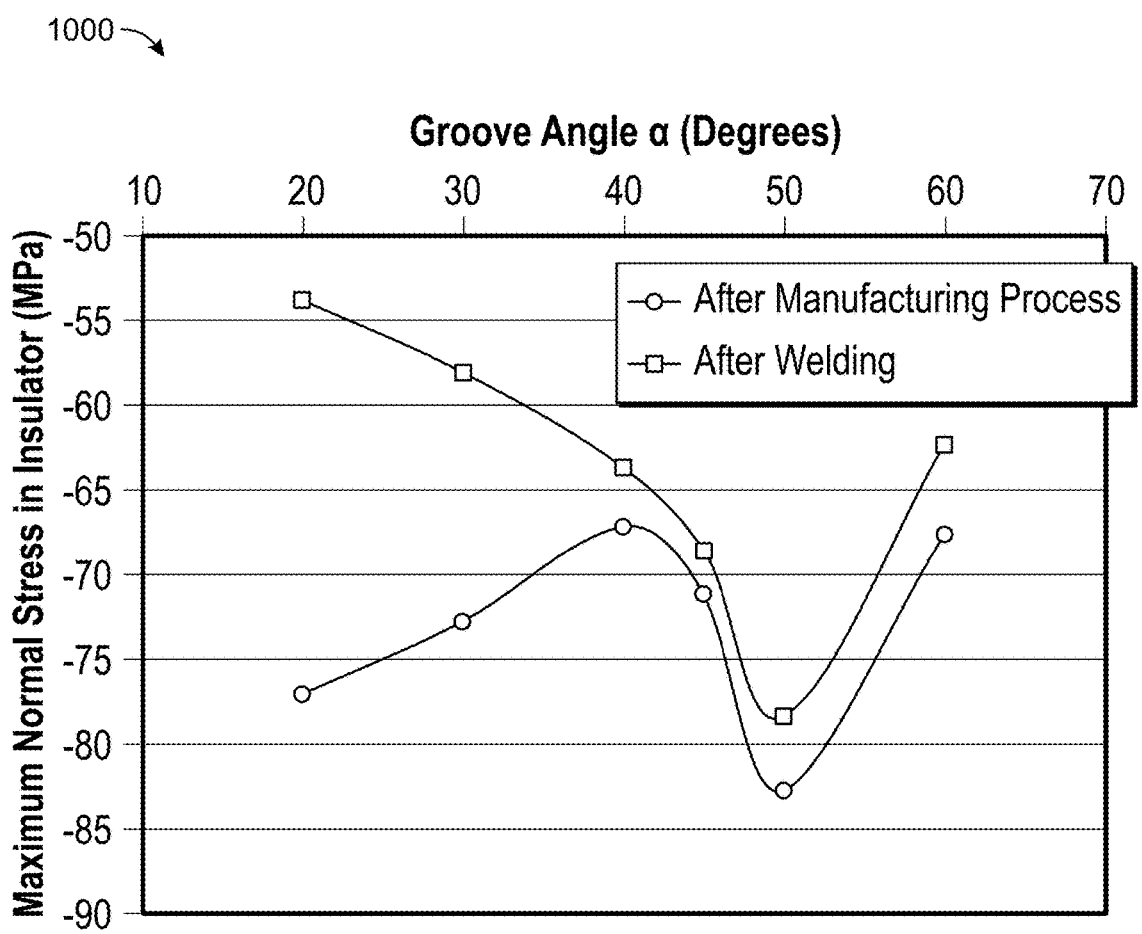
FIG. 10 is a graph showing groove angle vs. the maximum normal stress in the insulator, according to some embodiments.

FIG. 10 is a graph 1000 showing groove angle α vs. the maximum normal stress in the insulator 120, according to some embodiments. The groove angle α may also influence the strain/stress distributions within the insulator 120. To improve the stress distributions, the angle α may be from about 40° to about 60° or about 45° to about 55°.

Figure 11:
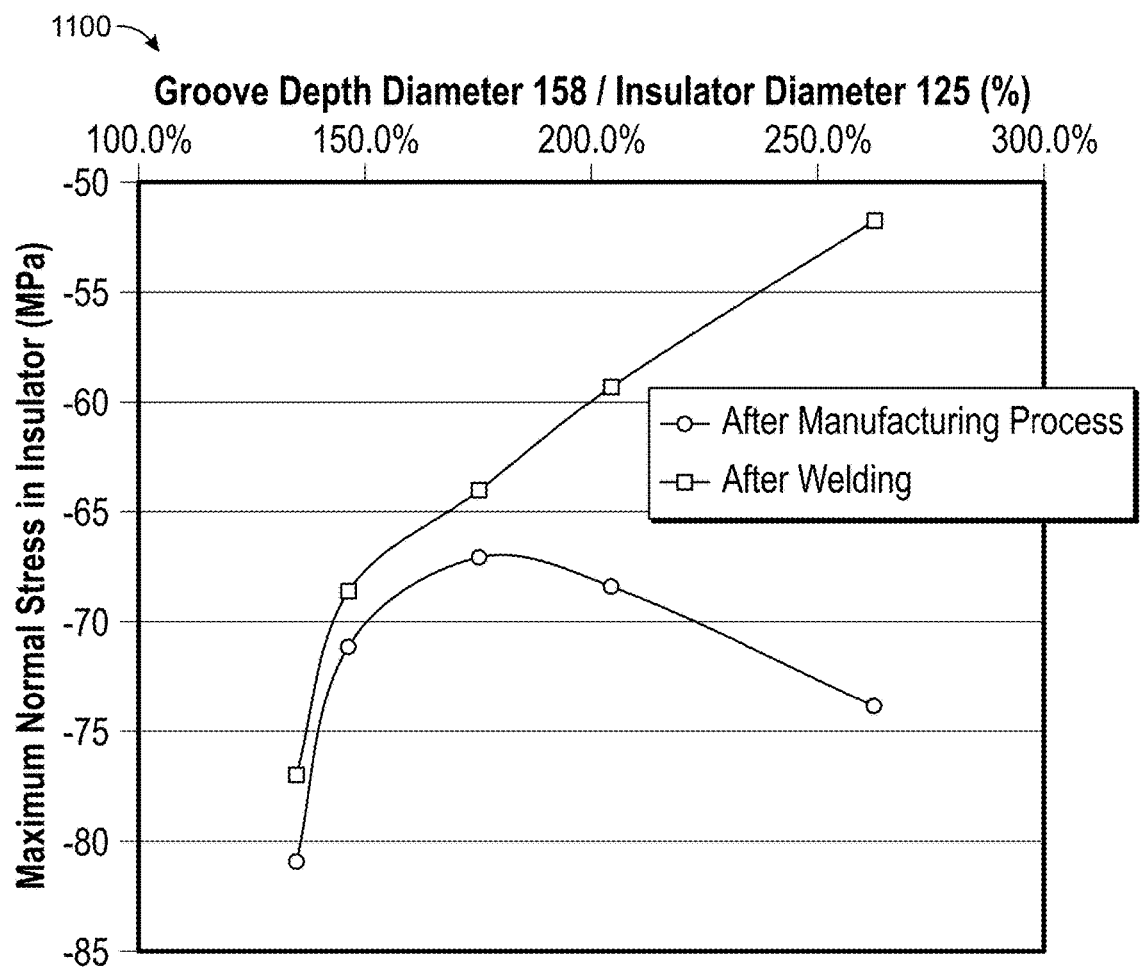
FIG. 11 is a graph showing groove depth diameter/insulator diameter vs. the maximum normal stress in the insulator, according to some embodiments.

FIG. 11 is a graph 1100 showing a ratio of the groove depth diameter 158 to the insulator diameter 125 vs. the maximum normal stress in the insulator 120, according to some embodiments. The ratio may also influence the strain/stress distributions within the insulator 120. To improve the stress distributions, the ratio may be from about 125% to about 150% or about 130% to about 140%.

As used herein, the terms "inner" and "outer"; "up" and "down"; "upper" and "lower"; "upward" and "downward"; "above" and "below"; "inward" and "outward"; and other like terms as used herein refer to relative positions to one another and are not intended to denote a particular direction or spatial orientation. The terms "couple," "coupled," "connect," "connection," "connected," "in connection with," and "connecting" refer to "in direct connection with" or "in connection with via one or more intermediate elements or members."

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. Moreover, the order in which the elements of the methods described herein are illustrate and described may be re-arranged, and/or two or more elements may occur simultaneously. The embodiments were chosen and described in order to best explain the principals of the invention and its practical applications, to thereby enable others skilled in the art to best utilize the invention and various embodiments with various modifications as are suited to the particular use contemplated.

What is claimed is:

1. An electrode configured to measure a frequency-dependent complex permittivity of a fluid, comprising:
   a conductor;
   an insulator positioned at least partially around the conductor, wherein an upper surface of the insulator is at least partially concave symmetrically about a central axis of the insulator; and
   a housing positioned at least partially around the insulator.

2. The electrode of claim 1, wherein the electrode is configured to reflect an electromagnetic wave, wherein an impedance between the conductor and the housing changes in response to the fluid wetting the insulator, causing an amplitude and a phase of the reflected electromagnetic wave to change, wherein the frequency-dependent complex permittivity of the fluid is determined based at least partially upon the change in the amplitude and the change in the phase, and wherein the frequency-dependent complex permittivity is configured to be used to determine a conductivity of water in the fluid, a salinity of water in the fluid, or a combination thereof.

3. The electrode of claim 1, wherein an inner radial portion of the upper surface is recessed from about 0.05 mm to about 0.5 mm respect to an outer radial portion of the upper surface.

4. The electrode of claim 3, wherein an upper surface of the conductor is substantially aligned with the inner radial portion of the upper surface of the insulator, and wherein the upper surface of the conductor is recessed with respect to the outer radial portion of the upper surface of the insulator.

5. The electrode of claim 1, wherein an upper surface of the housing is also at least partially concave, such that the upper surfaces of the insulator and the housing define a substantially inverted dome shape having a grinding diameter, and wherein a ratio of the grinding diameter to a ratio of a diameter of the insulator is from about 102% to about 122%.

6. The electrode of claim 1, wherein an outer surface of the housing has a groove that is symmetric at least on opposite sides of a central housing axis of the housing.

7. The electrode of claim 6, wherein:
the groove extends radially-inward toward the insulator, and
the groove extends around a circumference of the housing, wherein the groove is symmetric around the central housing axis.

8. The electrode of claim 1, wherein the insulator comprises glass, and the upper surface of the insulator being at least partially concave causes compression in the insulator.

9. An electrode configured to measure a frequency-dependent complex permittivity of a fluid, comprising:
a conductor;
an insulator positioned at least partially around the conductor; and
a housing positioned at least partially around the insulator, wherein an outer surface of the housing has a groove that is symmetric at least on opposite sides of a central housing axis of the housing.

10. The electrode of claim 9, wherein the electrode is configured to reflect an electromagnetic wave, wherein an impedance between the conductor and the housing changes in response to the fluid wetting the insulator, causing an amplitude and a phase of the reflected electromagnetic wave to change, wherein the frequency-dependent complex permittivity of the fluid is determined based at least partially upon the change in the amplitude and the change in the phase, and wherein the frequency-dependent complex permittivity is configured to be used to determine a conductivity of water in the fluid, a salinity of water in the fluid, or a combination thereof.

11. The electrode of claim 9, wherein the groove extends radially-inward toward the insulator, the groove extends around a circumference of the housing, and the groove is symmetric around the central housing axis.

12. The electrode of claim 9, wherein a first portion of the outer surface defining the groove is substantially perpendicular to a central longitudinal axis through the electrode, and wherein a second portion of the outer surface defining the groove is oriented at an angle from about 40° to about 60° with respect to the central longitudinal axis.

13. The electrode of claim 9, wherein a ratio of a groove depth diameter of the groove to a diameter of the insulator is from about 125% to about 150%.

14. The electrode of claim 9, wherein a distance between a central longitudinal axis through the electrode and an innermost radial surface of the housing defining the groove may be from about 100% to about 130% of a diameter of the insulator.

15. A method of producing an electrode, comprising:
positioning a conductor at least partially within an insulator;
positioning the insulator at least partially within a housing;
shrink-fitting the conductor, the insulator, and the housing, or a combination thereof together; and
forming a groove in an outer surface of the housing, wherein the groove is symmetric at least on opposite sides of a central housing axis of the housing.

16. The method of claim 15, wherein the electrode is configured to reflect an electromagnetic wave, wherein an impedance between the conductor and the housing changes in response to a fluid wetting the insulator, causing an amplitude and a phase of the reflected electromagnetic wave to change, wherein a frequency-dependent complex permittivity of the fluid is configured to be determined based at least partially upon the change in the amplitude and the change in the phase, and wherein the frequency-dependent complex permittivity is configured to be used to determine a conductivity of water in the fluid, a salinity of water in the fluid, or a combination thereof.

17. The method of claim 15, further comprising grinding an upper surface of the insulator to cause the upper surface to be at least partially concave symmetrically about a central axis of the insulator.

18. The method of claim 17, wherein an inner radial portion of the upper surface is recessed from about 0.05 mm to about 0.5 mm with respect to an outer radial portion of the upper surface, wherein an upper surface of the conductor is substantially aligned with the inner radial portion of the upper surface of the insulator, and wherein the upper surface of the conductor is recessed with respect to the outer radial portion of the upper surface of the insulator.

19. The method of claim 17, wherein the groove is formed in the housing before the upper surface of the insulator is grinded.

20. The method of claim 17, wherein the groove is formed in the housing after the shrink-fitting, and wherein the upper surface of the insulator is grinded after the shrink-fitting.

* * * * *